US009435496B2

(12) United States Patent
Moore

(10) Patent No.: US 9,435,496 B2
(45) Date of Patent: Sep. 6, 2016

(54) FULL SPECTRUM LED ILLUMINATOR

(71) Applicant: NOVADAQ TECHNOLOGIES INC., Mississauga (CA)

(72) Inventor: Frederick Allen Moore, Vancouver (CA)

(73) Assignee: Novadaq Technologies Inc., Mississauga (CA)

(*) Notice: Subject to any disclaimer, the term of this patent is extended or adjusted under 35 U.S.C. 154(b) by 0 days.

(21) Appl. No.: 14/658,869

(22) Filed: Mar. 16, 2015

(65) Prior Publication Data

US 2015/0184811 A1 Jul. 2, 2015

Related U.S. Application Data

(63) Continuation of application No. 13/415,561, filed on Mar. 8, 2012, now Pat. No. 8,979,301.

(60) Provisional application No. 61/450,360, filed on Mar. 8, 2011.

(51) Int. Cl.
*F21V 19/00* (2006.01)
*F21K 99/00* (2016.01)
(Continued)

(52) U.S. Cl.
CPC .............. *F21K 9/50* (2013.01); *A61B 1/063* (2013.01); *A61B 1/0638* (2013.01); *A61B 1/0684* (2013.01); *F21V 5/04* (2013.01); *F21V 9/08* (2013.01); *F21V 29/70* (2015.01);
(Continued)

(58) Field of Classification Search
CPC .............. F21K 9/50; F21V 5/04; F21V 9/08; F21V 29/70; A61B 1/0638; A61B 1/063; A61B 1/0684; F21Y 2101/025; F21Y 2113/005; F21Y 2101/02
See application file for complete search history.

(56) References Cited

U.S. PATENT DOCUMENTS 4,852,985 A 8/1989 Fujihara et al.
4,953,539 A 9/1990 Nakamura et al.
(Continued)

FOREIGN PATENT DOCUMENTS

JP H10-321005 A 12/1998
JP 2003-045210 A 2/2003
(Continued)

OTHER PUBLICATIONS

Oct. 1, 2014 Supplementary European Search Report issued in EP Application No. EP 12 75 4208.2.
(Continued)

*Primary Examiner* — Tracie Y Green
(74) *Attorney, Agent, or Firm* — Morrison & Foerster, LLP

(57) ABSTRACT

An apparatus for providing a light output to an optical guide for illumination of an imaged object including a plurality of solid state light-emitting sources each of which are independently powered and independently controlled, each light-emitting source emitting light at a wavelength which is different from the wavelength emitted by the other light-emitting sources. The apparatus also includes a heat sink configured to thermally couple the plurality of solid state light-emitting sources and provide conduction of heat generated by the plurality of solid state light-emitting sources. The apparatus further includes an optical elements to collect, collimate, and combine the emissions from the plurality of solid state light-emitting sources into a combined beam of light to be optically coupled to the light guide.

6 Claims, 2 Drawing Sheets

(51) Int. Cl.
*A61B 1/06* (2006.01)
*F21V 29/70* (2015.01)
*F21V 5/04* (2006.01)
*F21V 9/08* (2006.01)
*F21Y 101/02* (2006.01)
*F21Y 113/00* (2016.01)

(52) U.S. Cl.
CPC ..... *F21Y 2101/02* (2013.01); *F21Y 2101/025* (2013.01); *F21Y 2113/005* (2013.01)

(56) References Cited

U.S. PATENT DOCUMENTS

| | | |
|---|---|---|
| 6,226,126 B1 | 5/2001 | Conemac |
| 8,408,772 B2 | 4/2013 | Li |
| 2002/0076480 A1 | 6/2002 | Hsieh et al. |
| 2004/0149998 A1 | 8/2004 | Henson et al. |
| 2005/0140270 A1 | 6/2005 | Henson et al. |
| 2005/0280783 A1 | 12/2005 | Yamasaki et al. |
| 2006/0002141 A1 | 1/2006 | Ouderkirk et al. |
| 2006/0215406 A1 | 9/2006 | Thrailkill |
| 2007/0041195 A1 | 2/2007 | Chen |
| 2007/0091634 A1 | 4/2007 | Sakurada |
| 2008/0074752 A1 | 3/2008 | Chaves et al. |
| 2008/0208006 A1 | 8/2008 | Farr |
| 2008/0246920 A1 | 10/2008 | Buczek et al. |
| 2009/0040754 A1 | 2/2009 | Brukilacchio et al. |
| 2009/0153797 A1 | 6/2009 | Allon et al. |
| 2009/0201577 A1 | 8/2009 | LaPlante et al. |
| 2010/0110393 A1 | 5/2010 | Chen et al. |
| 2010/0208487 A1 | 8/2010 | Li |
| 2012/0044462 A1 | 2/2012 | Kaji |

FOREIGN PATENT DOCUMENTS

| | | |
|---|---|---|
| JP | 2006-087764 A | 4/2006 |
| JP | 2007-072392 A | 3/2007 |
| JP | 2010-117442 A | 5/2010 |
| WO | 94/13191 A1 | 6/1994 |

OTHER PUBLICATIONS

Jun. 27, 2014 Office Action issued in U.S. Appl. No. 13/415,561.
Oct. 23, 2013 Office Action issued in U.S. Appl. No. 13/415,561.
Mar. 9, 2015 Office Action issued in Japanese Patent Application No. 2013-557187.

FULL SPECTRUM LED ILLUMINATOR

BACKGROUND

The present disclosure relates to an illumination system, in particular for endoscopy, and more particularly a full spectrum illumination system using light-emitting diodes (LED) and/or semiconductor lasers.

Illumination systems for endoscopy, microscopy and similar optical imaging applications have for many years utilized arc lamp or halogen technology as the light source of choice. More recently, various forms of solid state light sources such as light emitting diodes or diode lasers have been introduced for use in some of these imaging applications. Due to the output brightness or output spectrum limitations of these solid state light sources, the use of LEDs and/or laser diodes has, until recently, been limited to optical imaging applications where low light levels are sufficient or where narrow spectrum illumination is required/desired.

Achieving sufficiently bright, full visible spectrum illumination with solid state light sources has remained challenging for a number of reasons.

a) Firstly, LED technology has been improving, but started far behind that of lamp technology in terms of total light output. Increasingly higher light outputs are now available, but light from a single phosphor-coated ("white") LED, for example, is still orders of magnitude below that of an arc lamp.

b) Alternatively light from multiple, different colored (e.g. red, green and blue) LEDs can be combined using dichroic mirrors to "source" emitting over a wide spectral range. The imaging applications mentioned above, however, generally require coupling light into liquid, fiberoptic, or rod lens light guides. Such optical light guides typically have both a small physical aperture with dimensions of a few mm across and a constrained/limited numerical aperture (NA). Moreover, etendue considerations rapidly constrain the practical implementation of such combined source illumination systems.

c) Should the etendue considerations with a multiple different colored LED arrangement be overcome by a suitable arrangement of sources and dichroics with optical path lengths that are carefully equalized, then other implementation issues arise with respect to effective cooling and cost.

Finally, although output brightness of red and blue LEDs has reached levels at which they can produce light with a brightness substantially equivalent to that of the red and blue portions of an arc lamp or a halogen lamp spectrum, the output of green LEDs tends to be substantially less than the green light produced by lamps.

It would therefore be desirable and advantageous to address this problem and to obviate other prior art shortcomings by providing a cost-effective and reliable illuminator utilizing solid state light sources to produce a bright, color balanced, broad spectrum visible light output that may be effectively coupled to an optical light guide. It would also be desirable to include in such illuminator and in the resulting light emission, other light sources for UV or NIR illumination (e.g. for fluorescence excitation of tissue).

SUMMARY

According to one aspect of the present disclosure, an illuminator is disclosed which utilizes solid state light sources to produce a bright, color balanced, broad-spectrum, visible light output.

According to one advantageous feature of the disclosure, the illuminator may contain multiple high power LED light sources that span the visible spectrum (e.g. from 400-700 nm). These LED light sources are separately powered and controlled. The light produced by these LEDs is combined into a single beam using either mirrors or dichroic filters appropriately wavelength matched to the LED light output. The combined light may then be coupled into an optical light guide using an appropriate optical element such as a high (e.g. >0.5) NA lens.

According to one advantageous feature of the disclosure, the illuminator may include LED light sources housed in discrete high thermal conductivity packages. The LED dies may be edge-emitting or surface emitting and they may be packaged in single or multi-die configurations.

According to one advantageous feature of the disclosure, the illuminator may contain a combination of red, green and blue LED light sources. Alternatively or in addition, one or more of these LED light sources may have other hues of the visible spectrum, including violet, yellow, amber/orange LEDs, as required or desirable for the application (e.g. in the endoscope). Alternatively, or in addition, a single LED package may contain any combination of these color dies.

According to one advantageous feature of the disclosure, to increase the green component of the emitted light and provide a more color balanced output, the illuminator may contain in addition to red and blue LED light sources at least two green LED light sources, such as a long wavelength green and a short wavelength green. The peak wavelengths and bandwidth of the two green LEDs is carefully selected to ensure that the combining optics produce maximum net green light output. In one embodiment the long wavelength green may have a peak wavelength at ~530 nm and an approximate FWHM bandwidth of +/−40 nm and the short wavelength green may have a peak wavelength at ~515 nm and an approximate FWHM bandwidth of +/−37 nm.

According to one advantageous feature of the disclosure, the LED light sources may be mounted on a heat sink in good thermal contact with a single heat spreader plate. The spreader plate may be a metal having high thermal conductivity, such as copper, aluminum, iron, diamond, gold or silver and the like. The spreader plate may be mounted on—or integral with—a passive cooling system, such as a finned heat sink or a heat pipe, or an active cooling system, such as a thermoelectric cooler (TEC) or liquid cooler. Thermal contact between the LEDs and the plate may be provided by, for example, soldering or with the application of a thermally conductive compound, such as Type 120 Silicon Thermal Joint Compound (Wakefield Thermal Solutions, New Hampshire). This mounting arrangement and cooling structure optimizes both cost/complexity of the assembly and cooling efficiency and therefore also the lifetime/reliability of the solid state source.

According to one advantageous feature of the disclosure, the LED light sources may be mounted on a plane which is common to the planar surface of the heat sink on the single heat spreader plate, with the optical path length increasing with wavelength, e.g. the red LED has longest optical path, the blue LED has shortest optical path. LED light source is positioned at or near the focal point of a compound collector group consisting of an aspheric lens (e.g., Newport KPA040-C, Irvine, Calif.), which collects the light from each LED light source. The collection efficiency of the aspheric lens may be enhanced by a field lens mounted between the LED and the aspheric lens. The aspheric lens projects a nearly collimated light beam from the LED onto a mirror or a dichroic filter (e.g. Semrock FF670-SDi01-25×36, Rochester, N.Y.) positioned to reflect light at a right angle relative to the light projected by the aspheric lens into the combined light beam path. The dichroic filter is designed to reflect substantially all light at or above the wavelength of the LED emission and transmits the light of all shorter wavelengths. The power and position of each aspheric lens and the power and position of any field lens is adjusted as required for each LED to accommodate the differences in optical path lengths. In this way, the etendue constraints with a linear arrangement of light sources can be managed and the capacity of the high NA lens in coupling the combined beam of light into an optical light guide can be maximized.

According to one advantageous feature of the disclosure, all optical elements not directly attached to the LED light sources (including all remaining collector lenses, reflective and dichroic mirrors, and collimating/condensing lenses) may be mounted in a mating mechanical enclosure. The enclosure may be fabricated from a single block of material such as aluminum, or similar material and may be machined or may be cast and machined as a single element. The mechanical enclosure may also be composed of multiple elements individually fabricated (e.g. machined) and assembled. The enclosure has a linear array of input ports matching the linear pattern of LED sources on the heat spreader plate—e.g., one input port for each LED light source—and a single output port. Once all optical components are mounted in the enclosure, the plate with the LED light sources is assembled to the enclosure input ports and a shutter that seals the exit aperture in the absence of a light guide is mounted placed on the output port. The enclosure is consequently fully sealed and the optical elements are protected against the ingress of dust and other contaminants.

According to one advantageous feature of the disclosure, the illuminator may utilize a design without lenses and have instead polished reflective surfaces that propagate the light emitted by the LEDs. The light can then, as before, be combined using dichroic filters, with the combined light being coupled into the optical light guide, by means of reflective surfaces.

According to one advantageous feature of the disclosure, the illuminator may also contain other light sources, such as one or more diode lasers, that are coupled into the combined optical path. In one embodiment, the diode lasers may be fiber coupled NIR lasers that emit in the 800-820 nm wavelength range suitable for fluorescence excitation of, for example, indocyanine green (ICG) or other NIR excited fluorescence agent. Alternatively or in addition, one or more of the fiber coupled diode lasers may produce 830 nm NIR light for purposes of mimicking the fluorescence of ICG. The NIR light emitted by the lasers may be coupled into the optical path by introducing an additional dichroic mirror that reflects NIR but transmits shorter wavelengths into the LED optical path. Alternatively, or in addition, the illuminator may contain one or more UV diode lasers for tissue autofluorescence excitation. These lasers may be coupled into the blue LED channel or directly coupled into the combined beam channel before the blue LED dichroic filter. The illuminator may also contain high powered NIR or UV LEDs instead of diode lasers.

The system also provides for imaging a conjugate plane from the collector group onto the light guide (i.e. fit a round cone to the light guide).

BRIEF DESCRIPTION OF THE DRAWINGS

Other features and advantages of the present invention will be more readily apparent upon reading the following description of currently preferred exemplified embodiments of the invention with reference to the accompanying drawing, in which.

DETAILED DESCRIPTION OF THE EMBODIMENTS

Figure 1:
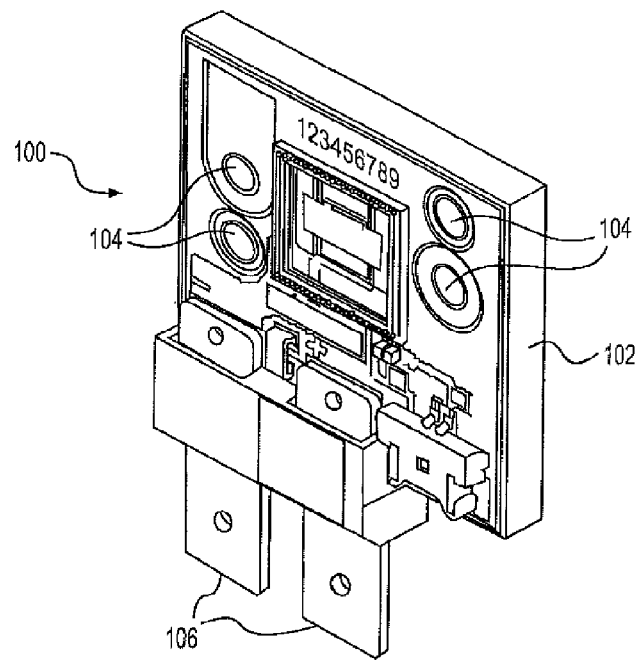
FIG. 1 shows an LED package with a highly thermally conductive substrate.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Figure 2:
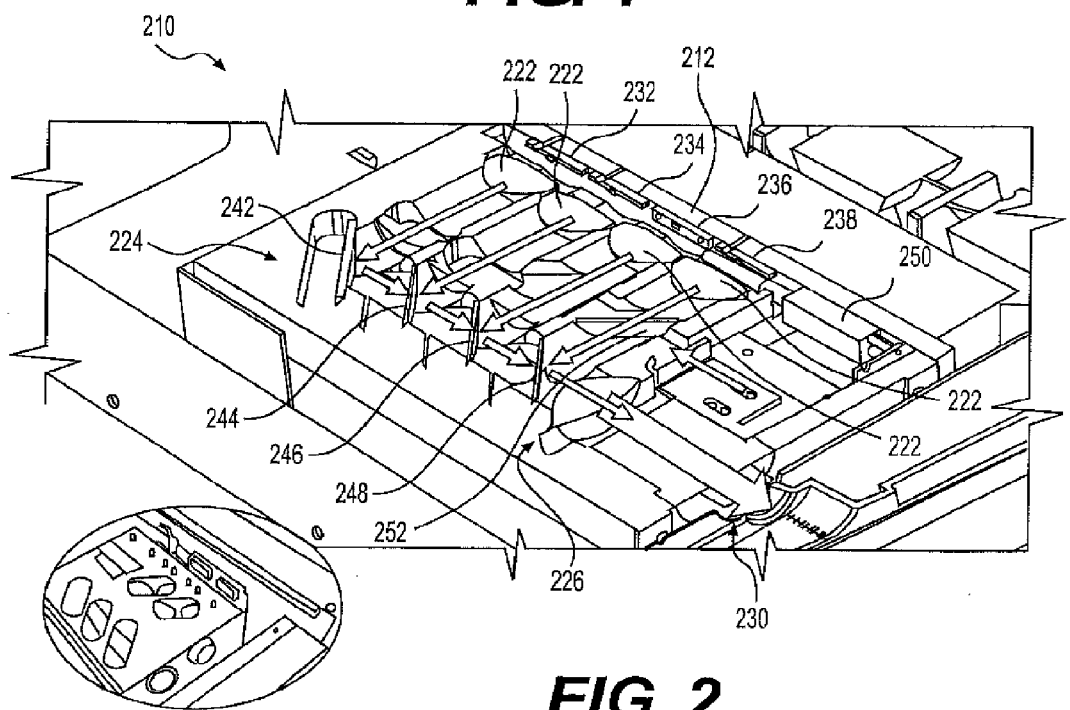
FIG. 2 shows in a cut-away view an illuminator with a linear array of LEDs arranged on a heat spreader, with collection, combining and condensing optics.

Turning now to the drawing, and in particular to FIG. 1, there is shown an LED package 100 including a substrate 102 with high thermal conductivity having mounting holes 104 for attachment to a heat spreader 212 shown in FIG. 2. The LED package also includes electrical terminals 106 for supplying electric power to the LEDs.

FIG. 2 shows in a cut-away view an illuminator 210 with a linear array of LEDs 232, 234, 236, 238 arranged on the heat spreader 212, with collector optics 222, combining optics 242, 244, 246, 248, and condensing optics 226. The LEDS 212 are arranged with increasing optical path lengths from a combined light output port 230. Collector optics 222, such as an aspheric lens and optionally a field lens, may be placed in front of each LED. The light from the red LED 232 is reflected at a 90° angle by a mirror 242. Additional dichroic mirrors 244, 246, 248 are placed in the combined beam path between this mirror 242 and the combined light output port 230. These dichroic mirrors 244, 246, 248 are designed to reflect, in the listed order, at a 90° angle light emitted by the exemplary long wavelength green LED 234 (peak wavelength at ~530 nm and approximate FWHM bandwidth of +/−40 nm), the exemplary short wavelength green LED 236 (peak wavelength at ~515 nm and approximate FWHM bandwidth of +/−37 nm), and the exemplary blue LED 238 (peak wavelength at ~460 nm and approximate FWHM bandwidth of +/−25 nm), while transmitting the wavelengths already present in the propagating combined beam, i.e., red, red+long green, red+long green+short green.

According to some exemplary embodiments, optical elements not directly attached to the LED light sources, for example, collector lenses, reflective and dichroic mirrors, and collimating/condensing lenses, may be mounted in a mating mechanical enclosure 224. The enclosure may be fabricated from a single block of material such as aluminum, or similar material, and may be machined or may be cast and machined as a single element. The mechanical enclosure may also be composed of multiple elements individually fabricated (e.g. machined) and assembled. The enclosure 224 has a linear array of input ports matching the linear pattern of LED sources 232, 234, 236, 238 on the heat spreader plate 212—e.g., one input port for each LED light source—and a single output port. Once all optical components are mounted in the enclosure 224, the heat spreader plate 212 with the LED light sources 232, 234, 236, 238 is assembled to the enclosure input ports.

The illuminator 210 may contain one or more other light sources, such as a diode laser 250, that are coupled into the combined optical path. The diode laser 250 may be a fiber-coupled NIR laser that emits in the 800-820 nm wavelength range suitable for fluorescence excitation of, for example, indocyanine green (ICG) or other NIR-excited fluorescence agent. Alternatively or additionally, a fiber-coupled diode laser may produce 830 nm NIR light for purposes of mimicking the fluorescence of ICG. As shown in FIG. 2, the NIR light emitted by the laser 250 may be coupled into the optical path by introducing an additional dichroic mirror 252 that reflects NIR but transmits shorter wavelengths into the LED optical path. Alternatively or additionally, the illuminator 210 may contain one or more UV diode lasers for tissue autofluorescence excitation. The aforementioned lasers may be coupled into the channel of the blue LED 238 or directly coupled into the combined beam channel before the blue LED dichroic filter 248. The illuminator 210 may also contain high powered NIR or UV LEDs instead of diode lasers.

Figure 3:
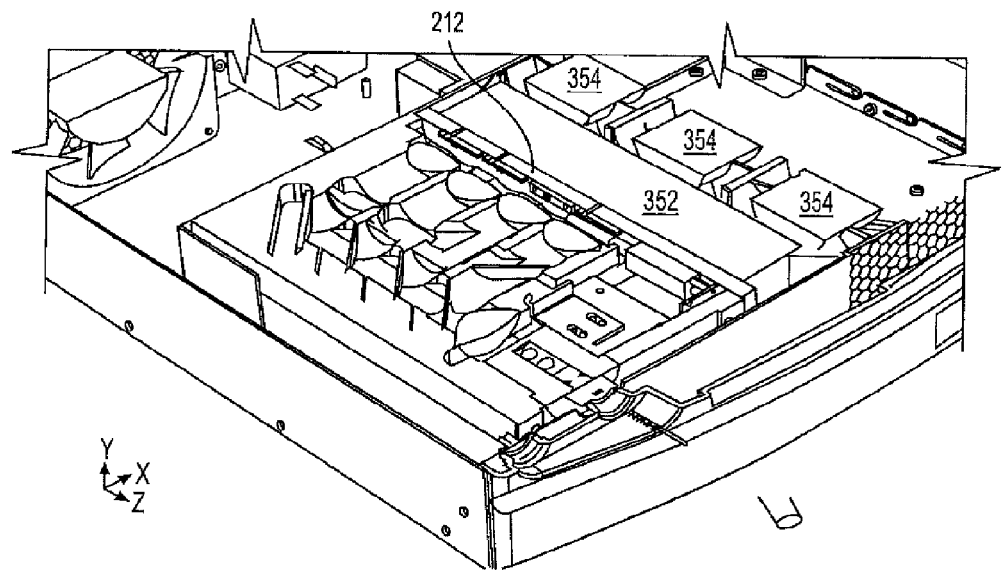
FIG. 3 shows in a cut-away view an illuminator with a linear array of LEDs arranged on a heat spreader, with heat exchanger and fans.

FIG. 3 shows schematically the illuminator in a cut-away view with the linear array of LEDs 232, 234, 236 on heat spreader 212, the LED-Laser heat exchanger (heat sink) 352, and the LED-Laser heat exchanger fans 354.

Figure 4:
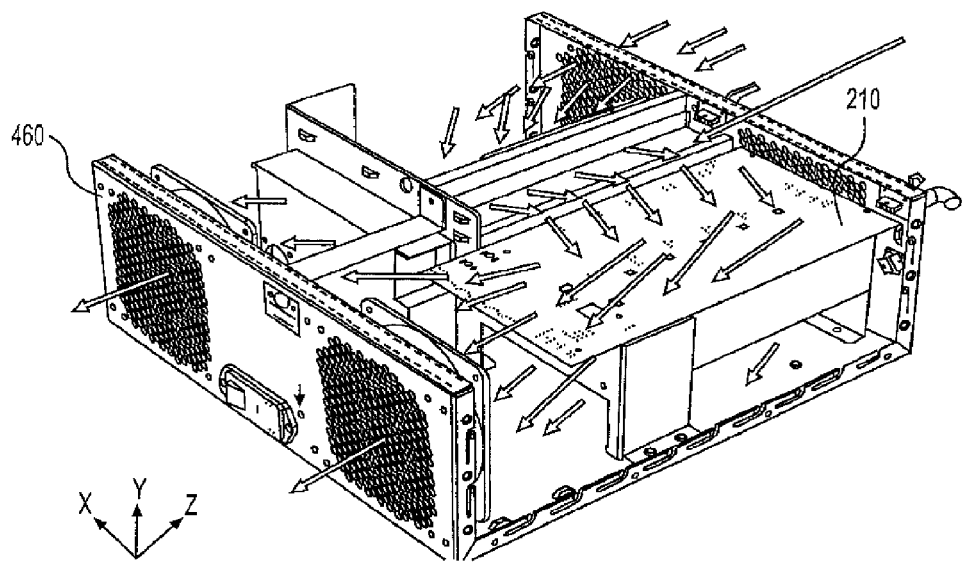
FIG. 4 shows an exemplary air flow pattern of the illuminator in an enclosure.

FIG. 4 shows schematically an exemplary air flow pattern around the illuminator 210 in the enclosure 460. FIG. 4 is a perspective view that differs from the view of FIG. 3, as shown by the X-Y-Z axis.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed is:

1. An apparatus for providing a light output to an optical guide for illumination of an object to be imaged, the apparatus comprising:
a plurality of solid state light-emitting sources each of which are independently powered and independently controlled, each light-emitting source emitting light at a wavelength that is different from a wavelength emitted by the other light-emitting sources;
a heat sink configured to thermally couple the plurality of solid state light-emitting sources and provide conduction of heat generated by the plurality of solid state light-emitting sources; and
optical elements configured to collect, collimate, and combine the emissions from the plurality of solid state light-emitting sources into a combined beam of light to be optically coupled to a light guide at an output of the apparatus,
wherein light emitted from each of the light-emitting sources travels an optical path length from the respective light-emitting source to the output, the optical path lengths from the light-emitting sources to the output increasing as the wavelength of the light emitted from the respective light-emitting source decreases from a nearest one of the light-emitting sources relative to the output to a farthest one of the light-emitting sources relative to the output.

2. The apparatus of claim 1, wherein the solid state light sources are selected from the group comprising light emitting diodes and diode lasers.

3. The apparatus of claim 1, wherein the optical elements include a field lens and an aspheric lens configured to collect and collimate the emission from each of the plurality of solid state light-emitting sources.

4. The apparatus of claim 1, further comprising a dichroic filter configured to couple the collimated emission from each of the plurality of solid state light-emitting sources into the combined beam of light directed along a common path to an output port.

5. The apparatus of claim 1, wherein the optical elements are arranged such that the optical path length of each of the plurality of solid state light-emitting sources increases as said wavelength decreases.

6. The apparatus of claim 1, wherein each of the plurality of solid state light-emitting sources is substantially at a focal point of a compound collector group.

* * * * *